Figure 1:
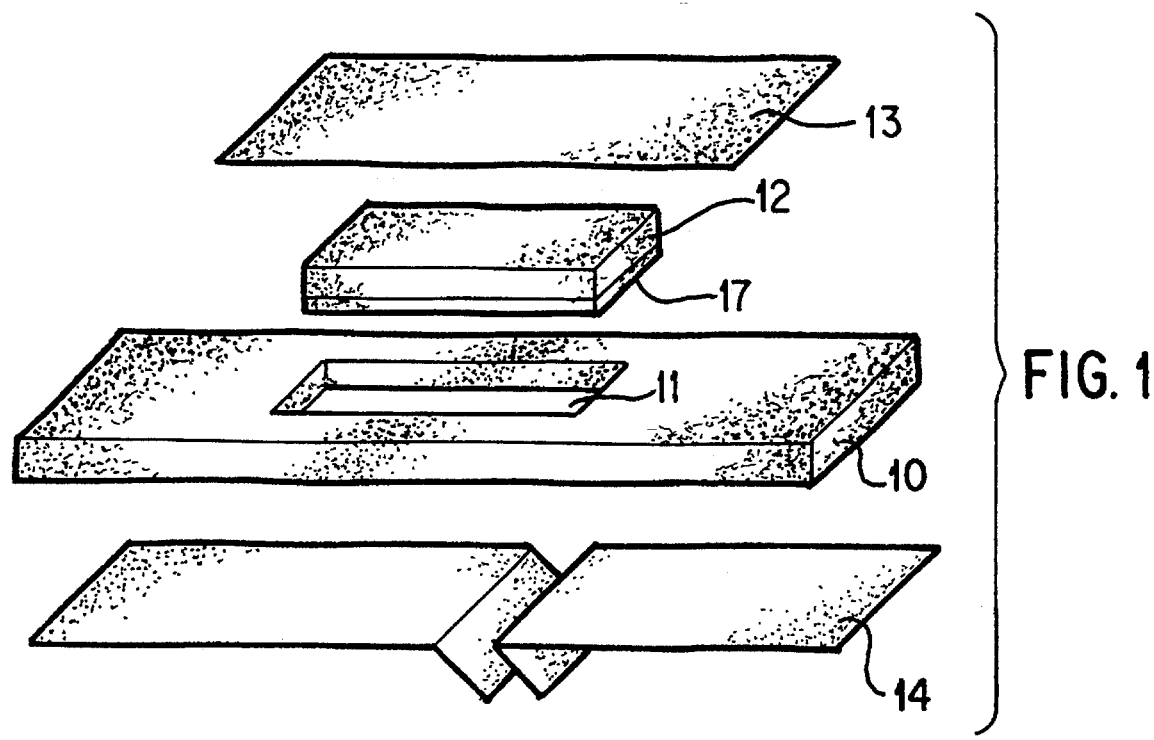

United States Patent [19]

Ewall

[11] Patent Number: 5,556,375
[45] Date of Patent: Sep. 17, 1996

[54] WOUND DRESSING HAVING A FENESTRATED BASE LAYER

[75] Inventor: Ralph Ewall, Newark, Del.

[73] Assignee: Hercules Incorporated, Wilmington, Del.

[21] Appl. No.: 260,583

[22] Filed: Jun. 16, 1994

[51] Int. Cl.$^6$ .................................................. A61F 13/00
[52] U.S. Cl. .............................. 602/58; 602/43; 602/54
[58] Field of Search ................................ 602/42, 43, 52, 602/53, 54, 57, 58, 59; 604/304, 307

[56] References Cited

U.S. PATENT DOCUMENTS

| | | |
|---|---|---|
| 3,367,329 | 2/1968 | Dibelius . |
| 3,419,006 | 12/1968 | King . |
| 3,645,835 | 2/1972 | Hodgson . |
| 3,664,343 | 5/1972 | Assarsson . |
| 3,888,247 | 6/1975 | Stenvall .................................. 128/155 |
| 3,972,328 | 8/1976 | Chen . |
| 3,993,551 | 11/1976 | Assarsson et al. . |
| 4,094,316 | 6/1978 | Nathanson . |
| 4,181,127 | 1/1980 | Linsky et al. ........................... 128/155 |
| 4,231,357 | 11/1980 | Hessner .................................. 128/156 |
| 4,281,650 | 8/1981 | Spiegelberg ............................. 602/57 |
| 4,413,621 | 11/1983 | McCracken et al. . |
| 4,477,325 | 10/1984 | Osburn . |
| 4,499,896 | 2/1985 | Heinecke ................................. 602/52 |
| 4,538,603 | 9/1985 | Pawelchak et al. . |
| 4,554,317 | 11/1985 | Behar et al. . |
| 4,554,371 | 11/1985 | Majoie . |
| 4,561,435 | 12/1985 | McKnight et al. ....................... 128/156 |
| 4,598,004 | 7/1986 | Heinecke . |
| 4,600,001 | 7/1986 | Gilman . |
| 4,638,797 | 1/1987 | Merrill et al. . |
| 4,641,643 | 2/1987 | Greer ..................................... 128/156 |
| 4,645,624 | 2/1987 | Ramm et al. . |
| 4,649,909 | 3/1987 | Thompson ............................... 128/156 |
| 4,657,006 | 4/1987 | Rawlings et al. . |
| 4,738,257 | 4/1988 | Meyer et al. . |
| 4,753,231 | 6/1988 | Lang et al. ............................. 128/156 |

(List continued on next page.)

FOREIGN PATENT DOCUMENTS

| | | |
|---|---|---|
| 0099758 | 2/1984 | European Pat. Off. . |
| 0106440 | 4/1984 | European Pat. Off. . |
| 0106439 | 4/1984 | European Pat. Off. . |
| 0174803 | 3/1986 | European Pat. Off. . |
| 0190814 | 8/1986 | European Pat. Off. . |
| 0236104 | 8/1987 | European Pat. Off. . |
| 0304536 | 3/1989 | European Pat. Off. . |
| 0410009 | 1/1991 | European Pat. Off. . |
| WO87/05206 | 9/1987 | WIPO . |

OTHER PUBLICATIONS

Article by Niinikoski et al., "Oxygen and Carbon Dioxide Tensions in Experimental Wounds", Surgery, Gynecology & Obstetrics, Dec. 71, vol. 133, pp. 1003–1007.

Balin et al., "The Effect of Oxygen Tension on the Growth & Metabolism of W1–38–Cells", J. Cell. Physic., 889, pp. 235–249.

Varghese et al., Local Environment of Chronic Wounds Under Synthetic Dressing; J. Arch. Dermatol., vol. 122; Jan. 1986; pp. 52–57.

Knighton et al., Oxygen Tension Regulates the Expression of Angiogenesis Factor by Macrophages, Science 1983, vol. 221, pp. 1283–1285.

Kaufman et al., The Microclimate Chamber: The Effect of Continuous Topical Admin. of 96% Oxygen . . . ; J. of Trauma, 1983; vol. 23, No. 9; pp. 806–815.

Hunt et al., The Effect of Varying Ambient Oxygen Tensions on Wound Metabolism & Collagen Synthesis; 1972, vol. 135, pp. 561–567.

Primary Examiner—Corrine M. McDermott
Assistant Examiner—Cris L. Rodriguez
Attorney, Agent, or Firm—Martin F. Sloan; Mark Goldberg

[57] ABSTRACT

An island wound dressing comprising a fenestrated base layer, an absorbent pad positioned in the base layer fenestration, and a liquid and microorganism impermeable, gas and moisture vapor permeable cover sheet.

20 Claims, 1 Drawing Sheet

U.S. PATENT DOCUMENTS

| | | | |
|---|---|---|---|
| 4,798,201 | 1/1989 | Rawlings et al. | 128/156 |
| 4,813,942 | 3/1989 | Alvarez | 604/290 |
| 4,875,473 | 10/1989 | Alvarez | 128/155 |
| 4,906,240 | 3/1990 | Reed et al. | 604/307 |
| 4,977,892 | 12/1990 | Ewall | 128/156 |
| 5,056,510 | 10/1991 | Gilman | 128/155 |
| 5,060,642 | 10/1991 | Gilman | 128/155 |
| 5,086,763 | 2/1992 | Hathman | |
| 5,092,323 | 3/1992 | Riedel et al. | 602/54 |
| 5,106,629 | 4/1992 | Cartmell et al. | 602/57 |
| 5,139,861 | 8/1992 | Williams et al. | 428/288 |
| 5,145,676 | 8/1992 | Fahey, III et al. | 425/85.1 |
| 5,244,457 | 9/1993 | Karaim et al. | 602/54 |
| 5,264,218 | 11/1993 | Rogozinski | |
| 5,308,313 | 5/1994 | Karami et al. | 602/55 |

WOUND DRESSING HAVING A FENESTRATED BASE LAYER

FIELD OF THE INVENTION

The present invention relates to an island wound dressing comprising an absorbent pad; a liquid and microorganism impermeable, gas and moisture vapor permeable cover sheet; and a fenestrated base layer.

BACKGROUND OF THE INVENTION

Ideally a wound dressing should adhere tightly and protect the wound from outside foreign matter, liquids and microorganisms. It should draw out exudate as it forms, while not totality desiccating the wound. Also the dressing should control the wound gas microenvironment during healing by allowing ingress of oxygen and egress of carbon dioxide at the appropriate rates. Many wound dressings are known that achieve a number of these properties.

U.S. Pat. Nos. 4,598,004; 3,645,835; 4,638,797; 4,600,001; and 4,413,621 describe wound dressings that function very well for shallow wounds with relatively low exudate levels. However, in general they are not ideal for highly exudative wounds, because they do not avoid exudate pooling under the dressing. Low exudate removal rate hydrogel dressings are also disclosed in U.S. Pat. Nos. 4,554,317; 3,419,006 3,993,551 and 3,664,343.

U.S. Pat. Nos. 4,645,624; 4,499,896 and 4,657,006 disclose pouch dressings that provide better exudate management. These dressings, however generally have poor skin adherence and do not handle the large volumes of exudate.

U.S. Pat. Nos. 3,972,328, 4,538,603, and EP 0,190,814 describe dressings consisting of rubber-based adhesives compounded with various absorbent materials, covered with impermeable film or foam sheets. These dressings absorb and hold the exudate. If left in place on highly exudative wounds, a significant amount of fluid is entrapped next to the wound, building up a significant undesirable pressure. These occlusive dressings often leak the entrapped fluid.

U.S. Pat. Nos. 4,477,325 and 4,738,257 describe modified occlusive rubber dressings that have decreased degradation of the rubber into the wound because of crosslinking of the rubber. Decreased skin adhesion results from the crosslinking, so that the dressings tend to leak exudate.

Many types of island dressings have been developed to better handle exudate. These island dressings have highly absorbent pads and transmit moisture vapor to the air. See U.S. Pat. Nos. 4,753,231; 4,181,127; 4,561,435 and 4,649,909. These dressings are not entirely satisfactory because of inadequate moisture vapor transmission to handle very high exudative wounds, and/or inadequate control of wound/gas environment.

Several patents disclose island dressings having some structural similarities to the dressings of the present invention. U.S. Pat. No. 4,231,357 discloses an island dressing having an absorbent pad in a liquid pervious envelope. This dressing relies on dressing changes, rather than moisture vaporization, for exudate removal. Leakage through the permeable envelope is a serious problem. The dressing does not attempt to deal with the wound gas microenvironment. U.S. Pat. No. 4,641,643 and EP 0236104 disclose island dressings having fenestrated base layers that may have therein an absorbent pad. The dressing of the U.S. Patent has a transparent film cover sheet that is hinged at one end so that it can be raised to give access to the wound for cleansing and medication. These references contain no disclosure concerning control of gas microenvironment.

A number of dressings have been described that are designed primarily for exudate removal. See EP 106,439; 106,440; and 174,803. These dressings do not enable the changing of the wound gas microenvironment without changing the entire dressing. They do not comprise a base layer that remains on the patient through a number of dressing changes. While these dressings can be used for low exudative wounds, they are not ideal for highly exudative wounds. Not only is exudate handling generally insufficient, but also these prior art dressings are not capable of controlling and varying the gas levels of the wound environment as healing progresses through wound healing phases.

Wound classification by stages is conventional. A Stage I wound is a shallow wound that penetrates into but not through the epidermis. A Stage II wound penetrates through the epidermis, and possibly into some subcutaneous tissue like fat, but not into muscle or bone.

Stages I and II type wound healing can be considered to take place through three healing phases. During initial Phase 1 of healing, high exudate withdrawal and high oxygen concentration are desirable. Phase 1 continues until angiogenesis has begun to restore blood flow to the wound.

During Phase 2, fibroblast migration and proliferation begin the generation of collagen and basement growth. Less exudate removal, but even greater concentrations of oxygen are desirable. This phase continues until re-epithelization has started.

The final Phase 3 of the wound healing involves the continuation and completion of re-epithelization, and wound approximation and closure. Low exudate removal is involved, but a very high oxygen concentration is desirable.

During the curing of Stage I and/or Stage II type wounds, a number of dressing changes normally are required during each healing phase, and different gas and water vapor permeabilities are desirable in each phase to provide appropriate wound microenvironments. Removal of the wound dressings from the site may damage the wound peripheral skin. It is therefore desirable to minimize the number of complete dressing changes, while being able to modify the wound microenvironment.

A wound dressing has been discovered that greatly minimizes the number of times the dressings must be removed from the skin, while enabling the modification of the dressing permeabilities during the healing process, thereby changing the wound microenvironment.

SUMMARY OF THE INVENTION

The present invention relates to a liquid and microorganism impermeable, moisture and gas permeable island wound dressing comprising a fenestrated base layer, an exudate-absorbing pad adjacent the wound, fitting into the base layer fenestration, and a liquid and microorganism impermeable, moisture and gas permeable cover sheet. The dressing passes exudate from the wound area, through the pad and cover sheet to be evaporated into the outside air as exudate is absorbed by the pad; and it passes adequate oxygen into the wound, and carbon dioxide out from the wound as it is formed. The base layer may remain on the patient through a number of pad and cover sheet changings, avoiding the trauma of frequent removal of the dressing from the skin.

DESCRIPTION OF THE INVENTION

The present invention wound dressing is an island dressing comprising a flexible, conformable base layer that is a barrier to liquids, gas and microorganisms. The base layer has a fenestration therein, shaped to surround the wound out of contact with the wound. The base layer adheres tightly to the intact substantially undamaged wound peripheral skin. The base layer may be left on the patient so long as it is functional, through a number of pad/cover sheet changes, up to 10 days or more.

Fitting snugly into the base layer fenestration is a liquid and gas highly permeable absorbent pad, positioned to be in liquid-conducting contact with the wound to absorb exudate. The pad has an inner wound-facing surface and an opposite outer surface away from the wound.

The dressing has a cover sheet parallel to, adjacent to, and covering the outer surface of the pad. The cover sheet is adhered to the periphery of the base layer fenestration. The cover sheet may cover the pad and extend beyond the periphery of the base layer fenestration, and be adhesively bonded directly to the outer side of the base layer. Alternatively the cover sheet may not extend beyond the base layer fenestration periphery. In such a dressing an outer attachment layer having a fenestration over most of the cover sheet is used, adhesively bonded to the periphery of the cover sheet and to the top side of the base layer fenestration periphery. Any conventional pressure sensitive adhesive (PSA) that is a barrier to liquids and microorganisms may be used to bond the attachment layer to the base layer.

Preferably, the wound-facing surface of the pad is treated with a non-adhering layer of material that is highly permeable to liquid and gas, which layer renders the pad non-adherent to the wound and does not substantially impede exudate absorption by the pad. The non-adhering layer can be a layer such as a polymeric net, mesh or perforated film, or a coating of non-stick material that does not significantly interfere with gas flow and exudate absorbation, such as a hydrogel material. A preferred non-adhering layer is "Delnet" P530 apertured polyolefin mesh (Applied Extrusion Technology, Inc.).

The cover sheet/pad/non-adhering layer can be made as a heat bonded laminate sheet material and cut to the desired size. A dressing with such a laminate that fits into the base layer fenestration requires a fenestrated outer attachment layer, to attach the laminate to the base layer.

For ease in handling before use, a conventional release liner covering the skin side of the dressing is used. W89-SP/P silicone coated release liner (a product of Mead Paper Products Co.) in an overlap or plowfold configuration is an excellent release liner.

Referring to the exploded view drawings, FIG. 1 shows the embodiment of the present invention wound dressing wherein the cover sheet 13 is the outermost layer, the dressing having no attachment layer. Base layer 10 will adhesively adhere to the skin of the patient. The fenestration 11 in the base layer 10 is sized so that absorbent pad 12 will fit snugly in fenestration 11 positioned to be in exudate conducting contact with the wound. Cover sheet 13, which is larger in area than pad 12, preferably is bonded to pad 12 and is adhesively bonded to the outer side of base layer 10. Non-adhering layer 17 is bonded to the wound-facing side of pad 12. Release liner 14 covers the wound side of base layer 10, and is readily removed before application to a patient.

Figure 2:
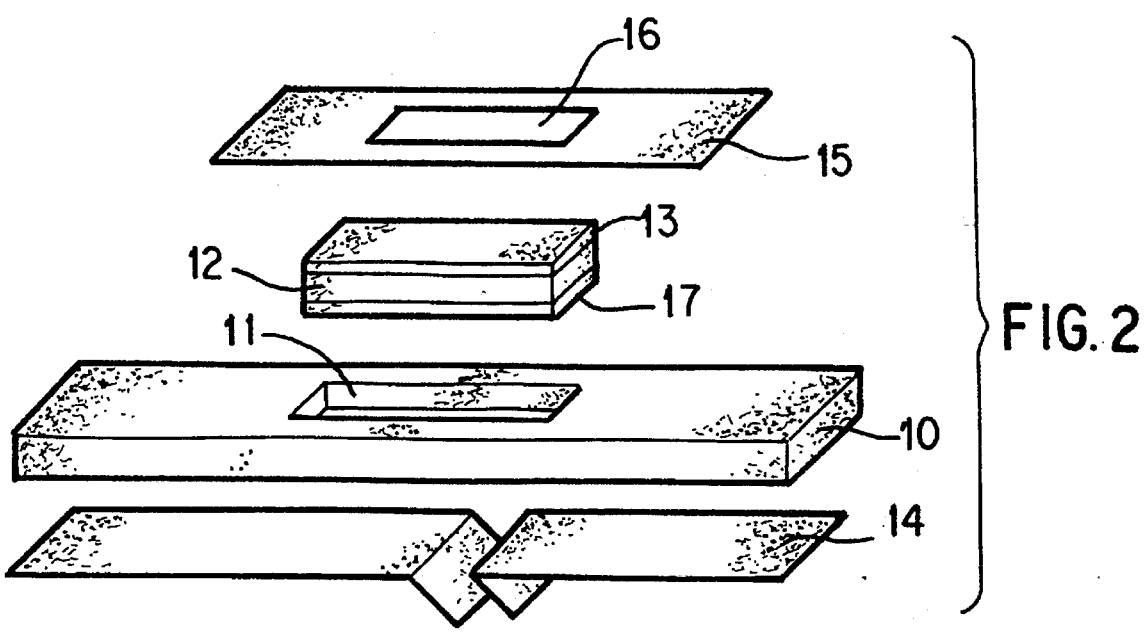

FIG. 2 shows the embodiment wherein cover sheet 13 is the same area as pad 12, to which it preferably is laminated. The laminate of cover sheet 13, pad 12 and non-adhering layer 17 fits into fenestration 11 of base layer 10. Release layer 14 covers the wound side of base layer 10. Attachment layer 15 has a fenestration 16 that is smaller in area than cover sheet 13, and is adhesively bonded to the periphery of cover sheet 13 and to the outer side of base layer 10.

The base layer can be made of any flexible conformable barrier sheet material. By "barrier" is meant that the base layer will not permit passage therethrough of significant amounts of liquids, gases or microorganisms. Preferably, the base layer is sufficiently moisture absorbent to absorb perspiration. It must adhere tightly to the skin surrounding the wound, and so may be itself adhesive or be coated on the wound-facing side with a microorganism and liquid impermeable high strength pressure sensitive adhesive. Many sheet materials of rubber, compounded rubber, and rubber adhesive, as well as other types of sheet materials, are commercially available and can be used for making the base layer. Excellent sheet materials are "Veriseal" A, A15 Mod. and A52 made by Veriseal Manufacturing Corp. The preferred base layer material is rubber adhesive compounded with absorbent material to take up fluids such as perspiration.

The absorbent pad contains one or more layers of absorbent material in adequate quantity to keep the wound substantially drained of exudate. The pad, and so the dressing, has an absorbency of from at least about 2 to about 20 cc of liquid/g of pad. Many non-toxic conventional known absorbent materials are readily available such as gauze, non-woven fabrics, fluff cellulosic pulps, synthetic polymer pulps, cotton, rayon and absorbent sponges. A preferred pad material is an intimate blend of cellulosic and synthetic fibrous material such as "Synpulp" 232.100 fluffed wood pulp blended with "Pulpex" polypropylene/polyethylene fibrous material treated with a wetting agent (Hercules Incorporated). The pad size and shape will vary with the size and shape of the wound. It should be large enough to cover the wound. Optionally, the pad can contain known absorbent particles. Also, the pad can contain medicaments, such as antibiotics and wound-healing stimulants.

The cover sheet is the dressing component essential for controlling the liquid and gas (oxygen and carbon dioxide) levels of the wound. Thus the cover sheet is liquid and microorganism impermeable, and permeable to moisture vapor, oxygen and carbon dioxide. The cover sheet is selected to have moisture vapor permeability rate (MVTR) and oxygen permeability that will enable the dressing to pass out and evaporate the desired aqueous portion of the exudate, and pass the appropriate amount of oxygen into the wound microenvironment while passing out carbon dioxide as it forms. Selecting a cover sheet with the correct permeabilities is the key to achieving the desired wound microenvironment, a feature of the present invention wound dressing.

The term "gas" as used herein, refers to oxygen and carbon dioxide. In practice, only the oxygen permeability of a cover sheet material is measured, because carbon dioxide permeabilities of cover sheets are much less critical. From a practical standpoint, if a cover sheet material has adequate oxygen permeability, it also has adequate carbon dioxide permeability.

Suitable polymeric films for use as the film cover sheets are listed in Table 1, along with the MVTRs and oxygen and carbon dioxide permeances for the films. Permeance is permeability per mil of film thickness.

TABLE 1

| FILM | MVTR | O₂PERM/CO₂PERM | | THICKNESS (MILS) |
|---|---|---|---|---|
| Microporous polyolefin PM-3 (Consolidated Thermoplastics Corp.) | 3800 | 21,700,000(a) | 21,700,000(a) | 0.8 |
| Microporous Polyolefin X025813-24-1 (Hercules Incorporated) | 950 | 8,640,000(a) | 8,640,000(a) | 4.8 |
| Microporous Polyolefin X-27448-44-4 (Hercules Incorporated) | 360 | 294,000 | 1,473,000 | 4.2 |
| Microporous Polyolefin X28244-13-4 (Hercules Incorporated) | 150 | 357,000 | 357,000 | 7.3 |
| Microporous Polyolefin X28244-13-4 (Hercules Incorporated) | 140 | 138,000 | 138,000 | 7.2 |
| Silicone (Surgitec Corp.) | — | >100,000 | 646,500 | 1.3 |
| Styrenebutadienestyrene (Consolidated Thermoplastics Corp.) | ~200 | 64,000 | 214,000 | 1.0 |
| Polyether block imide MF-827 (Bertek Corp.) | 2000 | 49,800 | — | 7.0 |
| Copolyester MF-3548 (Bertek Corp.) | 2175 | 33,800 | >20,000,000 | 1.5 |
| Polyurethane 946B (PCF-MED Corp.) | 1400 | 20,600 | 167,000 | 1.5 |
| Polyetherpolyurethane KH1391-02 (Semex Corp.) | 960 | 14,675 | 84,200 | 2.7 |
| Copolyester KM1353-06 (Semex Corp.) | 870 | 13,000 | 126,000 | 3.0 |
| Copolyester Med 5002 (Fasson Corp.) | 390 | 10,418 | — | 2.0 |
| Copolyester MF-325 (Bertek Corp.) | 300 | 9,600 | 111,500 | 0.7 |
| Low Density Polyethylene (USI Corp.) | ~30 | 2,800 | 12,000 | 3.0 |
| Polyesterpolyurethane KM1393-00 (Semex Corp.) | 330 | 1,270 | 10,200 | 4.0 |
| Cellophane P4T (Flexel Corp.) | 2300 | 17 | <40 | 1.5 |

(a.) measured by an experimental method for high permeable films.
Units for MVTR are g/sq.m./24 hrs. at ambient conditions of pressure, 25 deg. C. and 50% R.H.; and for $O_2$ and $CO_2$ Permeance are cc/sq.m./24 hrs./atm at 25 deg. C. and 50% R.H. Units of thickness are mils.

The following examples describe preferred embodiments of the present invention.

EXAMPLE 1

Wound dressings of the type shown in FIG. 1 are prepared by cutting "Veriseal" A52 rubber based adhesive sheet material ¼" thick into base layers 4"×4" having centered fenestrations 3"×3". Absorbent pads slightly smaller than 3"×3"×¼" are cut from batting of "Synpulp" 232.100 absorbent fibrous material, which has an absorbency of over 10 cc/g of pad. A non-adhering layer of "Delnet" P530 polyolefin net material is heat-bonded to the wound facing surface of each pad.

1 mil. thick cover sheets 3½"×3½" listed in Table 2 are heat-bonded to the outer sides of the pads, and adhesively bonded to the base layers.

TABLE 2

| Film No. | Film Type | O₂ Perm | MVTR |
|---|---|---|---|
| 94-1 | cellophane | 1 | 2500 |
| 94-2-15.3 | *microporous polypropylene | 15,300 | 360 |
| 94-2-17 | *microporous polypropylene | 17,000 | 360 |
| 94-2-20 | *microporous polypropylene | 20,000 | 360 |
| 94-3 | *microporous polypropylene | 23,000 | 400 |
| 94-4 | *microporous polypropylene | 87,000 | 700 |
| 94-5 | *microporous polypropylene | 7,000,000 | 950 |
| 94-6 | polyether block | 3,000 | 2000 |

TABLE 2-continued

| Film No. | Film Type | O₂ Perm | MVTR |
| --- | --- | --- | --- |
| | imide MF-827 (Bertek Corp) | | |

*biaxially oriented polypropylene film filled with powdered calcium carbonate to give the listed O$_2$ Perm. and MVTR, made by Hercules Incorporated. O$_2$ Permeance is (the permeability of a 1 mil. film). Units are cc/100 sq. in./24 hour day/atm; MVTR units are g/sq.in./24 hour day, at ambient pressure, each at 25° C. and 50% relative humidity.

These dressings are applied to full thickness skin wounds about 1.5 cm×1.5 cm in area on domestic white swine to evaluate the dressings' effectiveness during healing. The dressings are changed every three days for 21 days.

At 21 days no necrosis, edema or fatty infiltration is present in any of the wounds, and epithelization is complete in the majority of the wounds. Healing, using these present invention dressings, is very effective. Table 3 sets forth the percentage of healing after 21 days for the wounds treated with the present invention dressings.

TABLE 3

| | 21 DAY HEALING | |
| --- | --- | --- |
| Wound Site | Dressing Cover Sheet | 21 Day Healing |
| 1 | 94-1 | 94.20% |
| 2 | 94-2-15.3 | 96.24% |
| 3 | 94-3 | 98.49% |
| 4 | 94-4 | 96.03% |
| 5 | 94-5 | 92.15% |
| 6 | 94-6 | 94.84% |
| 7 | 94-1 | 96.96% |
| 8 | 94-2-17 | 96.48% |
| 9 | 94-3 | 96.70% |
| 10 | 94-4 | 99.55% |
| 11 | 94-5 | 95.30% |
| 12 | 94-6 | 97.23% |

The effectiveness of these dressings in treatment of these swine wounds demonstrates that the dressings are also effective for treating similar wounds in humans.

EXAMPLE 2

Wound dressings are prepared of the fenestrated attachment layer type dressing shown in FIG. 2, using the cover sheets of polymeric films listed in Table 4. The fenestrated attachment layer used in each dressing is 1 mil. polyester/polyurethane film coated with PSA, available from Gila River Corp. under the name 20LF Type II, cut to 4"×4" with a fenestration 2¾"×2¾". The base layers are prepared as in Example 1, 4"×4"×¼". Heat-bonded sheet material laminate of cover sheet/¼"pade/non-adhering layer is prepared and cut into squares slightly less than 3"×3". The pad material is "Synpulp" 232.100 and the non-adhering layer is "Delnet" P530. The pads have an absorbency of over 10 cc/g of pad. The exudate laminate is placed into the base layer fenestration and the attachment layer positioned thereover adhesively bonded to the cover sheet and base layer. The skin side of the base layer is covered with silicone-coated release liner W89-SP/P (available from Mead Paper Products) shaped in a plow-fold design. The sample dressings are packaged in peelable chevron pouches (available from Rollprint Packing Co. under the name Tyvek -EVA) and sterilized using gamma radiation, ready for use.

TABLE 4

| Sample* | O₂ Perm. (cc/m²/day/atm) | CO₂ Perm. (cc/m²/day/atm) | MVTR (cc/m²/day) | THICKNESS (MILS) |
| --- | --- | --- | --- | --- |
| | — | 21,700,000 | 3,800 | 0.8 |
| 2 | 64,000 | 216,000 | 200 | 1.0 |
| 3 | 49,800 | — | 2,000 | 1.0 |
| 4 | 33,800 | >20,000,000 | 2,175 | 1.5 |
| 5 | 20,600 | 167,500 | 1,400 | 1.5 |
| 6 | 14,675 | 84,200 | 960 | 2.7 |
| 7 | 13,000 | 126,500 | 870 | 3.0 |
| 8 | 10,418 | — | 390 | 2.0 |
| 9 | 9,600 | 111,500 | 300 | 0.7 |
| 10 | 2,800 | 12,000 | 30 | 3.0 |
| 11 | 1,270 | 10,200 | 330 | 0.4 |
| 12 | 17 | <40 | 2,500 | 1.5 |

*Sample 1-Microporous polyethylene film available under the name PM-3 from Consolidated Thermoplastics Corp.
Sample 2-Styrenebutadienestryrene film available from Consolidated Thermoplastic Corp.
Sample 3-Polyether block imide film available under the name MF-827 from Bertek Corp.
Sample 4-Copolyester film available under the name MF-3548 from Bertek Corp.
Sample 5-Polyurethane film available under the name 946B from PCF-Med Corp.
Sample 6-Polyetherpolyurethane film available under the name KM1391-02 from Semex Corp.
Sample 7-Copolvester Film available under the name KM1353-06 from Semex Corp.
Sample 8-Copolyester film available under the name Med 5002 from Fasson Corp.
Sample 9-Copolyester film available under the name MF-325 from Bertek Corp.
Sample 10-Low density polyethylene film
Sample 11-Polyesterpolyurethane film available under the name KM1393-00 from Semex Corp.
Sample 12-Cellophane film available under the name P4T from Flexel Corp.

These dressings are used to treat effectively Stage I human ulcer wounds.

Samples 9–12 are most effective only on shallow low exudative, and on partially healed, wounds.

EXAMPLE 3

Dressings are prepared according to Example 2. The cover sheets are 1.0 mil liquid and microorganism impermeable, gas permeable polyurethane film coated with PSA, obtained from Semex Corp. The absorbent pads are cut from ¼" polyurethane foam sheet material. The attachment layer is 20FL Type II film, the non-adhering layer is "Delnet" P530 mesh, and the base layer is "Veriseal" A52. The dressing components are the same size as in Example 1.

When evaluated by the INDA Demand Absorption Test, these dressings have absorptions of greater than 22.0 ml. in 24 hours. They are used with good results in treating highly exuding deep ulcer wounds.

EXAMPLE 4

Dressings are prepared according to the procedure and dimensions of Example 2. Cover sheets are 1.0 mil thick film of "Pebax" 827 polyether block imide (Bertek Corp.); and polyurethane (Semex Corp.). The absorbent pads are "Synpulp" 232.100 fibrous pulp, having "Delnet" P530 mesh non-adhering layers on wound-facing sides. The base layers are "Veriseal" STKS from Veriseal Manufacturing Corp.

These dressings have absorption values of 12–13 cc. at 24 hours, when under a constant counterweight of 700 grams. These results exceed the average output of deep ulcers (3–6 cc/day), and the absorption performance of the average occlusive dressings for such applications, (8–10 cc/day). These products are used in deep, highly exudative ulcers in humans with good results.

What is claimed:

1. A wound dressing comprising:
   (a) a flexible conformable base layer that is a barrier to liquids, gas and microorganisms, said base layer including a fenestration therein shaped to surround a wound out of contact therewith, said base layer comprising an upper surface and a lower surface;
   (b) an adhesive on said lower surface of said base layer for tightly adhering said base layer to skin surrounding the wound;
   (c) a liquid and gas permeable absorbent pad comprising a wound facing inner surface and an opposing outer surface, said pad being positioned within and surrounded by said fenestration in said base layer to be in contact with a wound; and
   (d) a cover sheet adjacent to and covering said outer surface of said pad, said cover sheet being adhered to said upper surface of said base layer around said fenestration and being impermeable to microorganisms and liquid and permeable to moisture vapor and gas.

2. The wound dressing according to claim 1, wherein said base layer comprises a rubber based material.

3. The wound dressing according to claim 2, wherein said rubber based material is compounded with an absorbent material.

4. The wound dressing according to claim 1, wherein said adhesive comprises a rubber based adhesive layer.

5. The wound dressing according to claim 1, comprising a release layer covering said adhesive and said inner surface of said pad.

6. The wound dressing according to claim 1, wherein said cover sheet is adhered to said upper surface of said base layer by adhesive bonding.

7. The wound dressing according to claim 1, wherein said pad comprises an absorbency of at least about 2 to 20 cc/g of pad.

8. The wound dressing according to claim 1, wherein said pad is substantially non-adherent to the wound.

9. The wound dressing according to claim 8, comprising a liquid and gas permeable non-adhering layer on the inner surface of said pad.

10. The wound dressing according to claim 9, wherein said non-adhering layer comprises a perforate film, net or mesh material that does not substantially impede exudate absorption by said pad.

11. The wound dressing according to claim 1, wherein said pad comprises at least one member selected from the group consisting of synthetic polymer pulp and cellulosic pulp.

12. The wound dressing according to claim 1, wherein said cover sheet is parallel to said pad.

13. A wound dressing comprising:
   (a) a flexible conformable base layer that is a barrier to liquids, gas and microorganisms, said base layer including a first fenestration therein shaped to surround a wound out of contact therewith, said base layer comprising an upper surface and a lower surface;
   (b) an adhesive on said lower surface of said base layer for tightly adhering said base layer to skin surrounding the wound;
   (c) a liquid and gas permeable absorbent pad comprising a wound facing inner surface and an opposing outer surface,
   (d) a cover sheet adjacent to and covering said outer surface of said pad, said cover sheet being impermeable to microorganisms and liquid and permeable to moisture vapor and gas;
   (e) said pad and said cover sheet being positioned within and surrounded by said first fenestration in said base layer so that said inner surface of said pad is positioned to be in contact with a wound; and
   (f) an outer attachment layer including a second fenestration therein, said cover sheet comprising a periphery, and said outer attachment layer is bonded to the periphery of said cover sheet and to the upper surface of said base layer so that said cover sheet is positioned below said second fenestration.

14. The wound dressing according to claim 13, wherein said base layer comprises a rubber based material.

15. The wound dressing according to claim 13, wherein said adhesive comprises a rubber based adhesive layer.

16. The wound dressing according to claim 15, comprising a release layer covering said adhesive layer and said inner surface of said pad.

17. The wound dressing according to claim 13, wherein said pad comprises an absorbency of at least about 2 to 20 cc/g of pad.

18. The wound dressing according to claim 13, wherein said pad is substantially non-adherent to the wound.

19. The wound dressing according to claim 18, comprising a liquid and gas permeable non-adhering layer on the inner surface of said pad.

20. The wound dressing according to claim 13, wherein said pad comprises at least one member selected from the group consisting of synthetic polymer pulp and cellulosic pulp.

* * * * *